US008268346B2

(12) United States Patent
Simes et al.

(10) Patent No.: US 8,268,346 B2
(45) Date of Patent: Sep. 18, 2012

(54) METHODS OF TREATING HOT FLASHES WITH FORMULATIONS FOR TRANSDERMAL OR TRANSMUCOSAL APPLICATION

(75) Inventors: Stephen M. Simes, Long Grove, IL (US); Leah M. Lehman, Green Oaks, IL (US)

(73) Assignee: Antares Pharma IPL AG, Zug (CH)

( * ) Notice: Subject to any disclaimer, the term of this patent is extended or adjusted under 35 U.S.C. 154(b) by 1178 days.

(21) Appl. No.: 11/737,389

(22) Filed: Apr. 19, 2007
(Under 37 CFR 1.47)

(65) Prior Publication Data
US 2008/0025920 A1 Jan. 31, 2008

Related U.S. Application Data

(60) Provisional application No. 60/794,015, filed on Apr. 21, 2006.

(51) Int. Cl.
*A61K 39/00* (2006.01)
*A61K 31/56* (2006.01)

(52) U.S. Cl. ........................................ 424/449; 514/182
(58) Field of Classification Search .................. 424/449; 514/182
See application file for complete search history.

(56) References Cited

U.S. PATENT DOCUMENTS

| | | | |
|---|---|---|---|
| 2,990,332 A | 6/1961 | Keating | 167/65 |
| 3,143,465 A | 8/1964 | Keating | 167/65 |
| 3,989,816 A | 11/1976 | Rajadhyaksha | 424/60 |
| 4,082,881 A | 4/1978 | Chen et al. | 514/39 |
| 4,221,778 A | 9/1980 | Raghunathan | 424/31 |
| 4,315,925 A | 2/1982 | Hussain et al. | 514/177 |
| 4,316,893 A | 2/1982 | Rajadhyakshan | 424/180 |
| 4,383,993 A | 5/1983 | Hussain et al. | 514/177 |
| 4,390,532 A | 6/1983 | Stuttgen et al. | 514/56 |
| 4,405,616 A | 9/1983 | Rajadhyaksha | 424/60 |
| 4,537,776 A | 8/1985 | Cooper | 514/424 |
| 4,557,934 A | 12/1985 | Cooper | 424/128 |
| 4,568,343 A | 2/1986 | Leeper et al. | 604/896 |
| 4,597,961 A | 7/1986 | Etscorn | 424/448 |
| 4,704,406 A | 11/1987 | Stanislaus et al. | 514/570 |
| 4,764,381 A | 8/1988 | Bodor et al. | 424/449 |
| 4,783,450 A | 11/1988 | Fawzi et al. | 514/78 |
| 4,808,411 A | 2/1989 | Lu et al. | 424/441 |
| 4,832,953 A | 5/1989 | Campbell et al. | 424/448 |
| 4,863,970 A | 9/1989 | Patel et al. | 514/784 |
| 4,883,660 A | 11/1989 | Blackman et al. | 424/78 |
| 4,952,560 A | 8/1990 | Kigasawa et al. | 514/2 |
| 4,956,171 A | 9/1990 | Chang | 424/449 |
| 4,973,468 A | 11/1990 | Chiang et al. | 424/449 |
| 5,041,439 A | 8/1991 | Kasting et al. | 514/227.2 |
| 5,053,227 A | 10/1991 | Chiang et al. | 424/448 |
| 5,059,426 A | 10/1991 | Chiang et al. | 424/449 |
| 5,071,657 A | 12/1991 | Oloff et al. | 424/486 |
| 5,112,842 A | 5/1992 | Zierenberg et al. | 514/367 |
| 5,128,138 A | 7/1992 | Blank | 424/449 |
| 5,134,127 A | 7/1992 | Stella et al. | 514/58 |
| 5,164,190 A | 11/1992 | Patel et al. | 424/448 |
| 5,178,879 A | 1/1993 | Adekunle et al. | 424/484 |
| 5,188,825 A | 2/1993 | Hes et al. | 424/78.1 |
| 5,225,189 A | 7/1993 | Pena | 424/70 |
| 5,230,896 A | 7/1993 | Yeh et al. | 424/443 |
| 5,232,703 A | 8/1993 | Blank | 424/449 |
| 5,238,933 A | 8/1993 | Catz et al. | 514/236.2 |
| 5,278,176 A | 1/1994 | Lin | 514/343 |
| 5,352,457 A | 10/1994 | Jenkins | 424/448 |
| 5,371,005 A | 12/1994 | Fujishiro et al. | 435/190 |
| 5,376,645 A | 12/1994 | Stella et al. | 514/58 |
| 5,453,279 A | 9/1995 | Lee et al. | 424/448 |
| 5,527,832 A | 6/1996 | Chi et al. | 514/772.4 |
| 5,532,278 A | 7/1996 | Aberg et al. | 514/617 |
| 5,580,574 A | 12/1996 | Behl et al. | 424/449 |
| 5,601,839 A | 2/1997 | Quan et al. | 424/448 |
| 5,602,017 A | 2/1997 | Fujishiro et al. | 435/190 |
| 5,603,947 A | 2/1997 | Wong et al. | 424/448 |
| 5,629,021 A | 5/1997 | Wright | 424/489 |
| 5,633,008 A | 5/1997 | Osborne et al. | 424/448 |
| 5,658,587 A | 8/1997 | Santus et al. | 424/448 |
| 5,660,839 A | 8/1997 | Allec et al. | 424/401 |

(Continued)

FOREIGN PATENT DOCUMENTS

EP      0 249 397 A2    12/1987

(Continued)

OTHER PUBLICATIONS

BioSante Pharmaceuticals (http:/www.drugs.com/nda/elestrin_060216.html (Feb. 16, 2006).*

(Continued)

*Primary Examiner* — Marcos Sznaidman
(74) *Attorney, Agent, or Firm* — Winston & Strawn LLP (57) ABSTRACT

The present invention relates generally to methods for treating hot flashes by administering formulations for transdermal or transmucosal administration of estrogen. The formulations of the invention are effective at treating hot flashes at surprisingly low daily doses, preferably the lowest effective dose of estrogen to treat hot flashes, e.g., about 0.45 to about 0.6 mg of estrogen per day. The amount of estrogen which is administered produces an estimated nominal daily estrogen dose in a subject undergoing treatment of from about 10 to about 15 micrograms, and a serum estradiol level of between about 25 pg/ml to about 50 pg/ml. The preferred formulations are substantially free of malodorous, and irritation causing long-chain fatty alcohols, long-chain fatty acids, and long-chain fatty esters.

4 Claims, 3 Drawing Sheets

U.S. PATENT DOCUMENTS

| | | | |
|---|---|---|---|
| 5,662,890 A | 9/1997 | Punto et al. | 424/59 |
| 5,665,560 A | 9/1997 | Fujishiro et al. | 435/11 |
| 5,677,346 A | 10/1997 | Aberg et al. | 51/617 |
| 5,716,638 A | 2/1998 | Touitou | 424/450 |
| 5,719,197 A | 2/1998 | Kanios et al. | 514/772.6 |
| 5,731,303 A | 3/1998 | Hsieh | 514/183 |
| 5,736,577 A | 4/1998 | Aberg et al. | 514/617 |
| 5,783,207 A | 7/1998 | Stanley et al. | 424/440 |
| 5,785,991 A | 7/1998 | Burkoth et al. | 424/448 |
| 5,798,242 A | 8/1998 | Fujishiro et al. | 435/190 |
| 5,814,659 A | 9/1998 | Elden | 514/452 |
| 5,831,035 A | 11/1998 | Timms | 530/389.1 |
| 5,834,010 A | 11/1998 | Quan et al. | 424/448 |
| 5,843,482 A | 12/1998 | Rhodes et al. | 424/653 |
| 5,846,983 A | 12/1998 | Sandborn et al. | 514/343 |
| 5,855,905 A | 1/1999 | Oettel et al. | 424/426 |
| 5,855,920 A | 1/1999 | Chein | 424/568 |
| 5,891,462 A | 4/1999 | Carrara | 424/449 |
| 5,900,250 A | 5/1999 | Lee et al. | 424/448 |
| 5,904,931 A | 5/1999 | Lipp et al. | 424/449 |
| 5,922,349 A | 7/1999 | Elliesen et al. | 424/449 |
| 5,932,243 A | 8/1999 | Fricker et al. | 424/450 |
| 5,935,604 A | 8/1999 | Illum | 424/501 |
| 5,945,405 A | 8/1999 | Spanton et al. | 514/29 |
| 5,968,919 A | 10/1999 | Samour et al. | 514/177 |
| 6,008,192 A | 12/1999 | Al-Razzak et al. | 514/11 |
| 6,034,079 A | 3/2000 | Sanberg et al. | 514/225.8 |
| 6,060,077 A | 5/2000 | Meignant | 424/434 |
| 6,071,959 A | 6/2000 | Rhodes et al. | 514/535 |
| 6,096,733 A | 8/2000 | Lubkin | 514/182 |
| 6,123,961 A | 9/2000 | Aberg | 424/468 |
| 6,124,355 A | 9/2000 | Guittard et al. | 514/534 |
| 6,133,248 A | 10/2000 | Stella | 514/58 |
| 6,153,216 A | 11/2000 | Cordes et al. | 424/449 |
| 6,165,497 A | 12/2000 | Osborne et al. | 424/448 |
| 6,166,044 A | 12/2000 | Sandborn et al. | 514/343 |
| 6,180,803 B1 | 1/2001 | Piasco et al. | 552/510 |
| 6,238,689 B1 | 5/2001 | Rhodes et al. | 424/436 |
| 6,267,985 B1 | 7/2001 | Chen et al. | 424/451 |
| 6,284,234 B1 | 9/2001 | Niemiec et al. | 424/78.07 |
| 6,299,900 B1 | 10/2001 | Reed et al. | 424/449 |
| 6,309,843 B1 | 10/2001 | Timms | 435/7.1 |
| 6,319,913 B1 | 11/2001 | Mak et al. | 514/179 |
| 6,383,471 B1 | 5/2002 | Chen et al. | 424/45 |
| 6,417,205 B1 | 7/2002 | Cooke et al. | 514/343 |
| 6,426,078 B1 | 7/2002 | Bauer et al. | 424/401 |
| 6,432,446 B2 | 8/2002 | Aberg | 424/468 |
| 6,440,454 B1 | 8/2002 | Santoro et al. | 424/449 |
| 6,444,234 B1 | 9/2002 | Kirby et al. | 424/725 |
| 6,465,005 B1 | 10/2002 | Biali et al. | 424/449 |
| 6,476,012 B2 | 11/2002 | Hochberg | 514/182 |
| 6,479,076 B2 | 11/2002 | Blank | 424/484 |
| 6,497,897 B2 | 12/2002 | Hidaka et al. | 424/449 |
| 6,503,894 B1 | 1/2003 | Dudley et al. | 514/178 |
| 6,545,046 B2 | 4/2003 | Sherratt et al. | 514/534 |
| 6,586,000 B2 | 7/2003 | Luo et al. | 424/449 |
| 6,596,740 B2 | 7/2003 | Jones | 514/343 |
| 6,743,441 B2 | 6/2004 | Sanders et al. | 424/448 |
| 6,818,226 B2 | 11/2004 | Reed et al. | 424/449 |
| 6,828,336 B2 | 12/2004 | Walling | 514/343 |
| 6,911,475 B1 | 6/2005 | Cesaro et al. | 514/567 |
| 6,923,983 B2 | 8/2005 | Morgan et al. | 424/448 |
| 6,929,801 B2 | 8/2005 | Klose et al. | 424/448 |
| 6,951,846 B2 | 10/2005 | Hartell et al. | 514/58 |
| 6,995,265 B2 | 2/2006 | Comins et al. | 546/14 |
| 7,029,692 B1 | 4/2006 | Bracht | 424/449 |
| 7,087,241 B2 | 8/2006 | Sanders et al. | 424/449 |
| 7,198,801 B2 | 4/2007 | Carrara et al. | 424/449 |
| 7,214,381 B2 | 5/2007 | Carrara et al. | 424/400 |
| 2001/0023261 A1 | 9/2001 | Ryoo | 514/772 |
| 2001/0031787 A1 | 10/2001 | Hsu et al. | 514/534 |
| 2001/0033870 A1 | 10/2001 | Luo et al. | 424/688 |
| 2001/0038855 A1 | 11/2001 | Desjardin et al. | |
| 2002/0147236 A1 | 10/2002 | Sanders et al. | 514/540 |
| 2002/0183296 A1 | 12/2002 | Dudley et al. | 514/177 |
| 2003/0022877 A1 | 1/2003 | Dudley | 514/177 |
| 2003/0050292 A1 | 3/2003 | Dudley et al. | 514/177 |
| 2003/0095926 A1 | 5/2003 | Dugger, III | 424/43 |
| 2003/0139384 A1 | 7/2003 | Dudley | 514/177 |
| 2003/0143278 A1 | 7/2003 | DiPiano et al. | 424/489 |
| 2003/0147926 A1 | 8/2003 | Ebert et al. | 424/400 |
| 2003/0175329 A1 | 9/2003 | Azarnoff et al. | 424/449 |
| 2003/0181430 A1 | 9/2003 | Gray et al. | 514/170 |
| 2003/0199426 A1 | 10/2003 | Carrara et al. | 514/2 |
| 2003/0222105 A1 | 12/2003 | Lee et al. | 222/382 |
| 2003/0232072 A1 | 12/2003 | Dudley et al. | 424/449 |
| 2004/0002482 A1 | 1/2004 | Dudley et al. | 514/169 |
| 2004/0139990 A1 | 7/2004 | Wachter et al. | 134/25.4 |
| 2004/0198706 A1 | 10/2004 | Carrara et al. | 514/169 |
| 2004/0213744 A1 | 10/2004 | Lulla et al. | 424/45 |
| 2005/0142175 A1 | 6/2005 | Langguth et al. | 424/449 |
| 2006/0027278 A1 | 2/2006 | Kurmis | 140/123.5 |
| 2007/0048360 A1 | 3/2007 | Carrara et al. | 424/443 |
| 2007/0098775 A1 | 5/2007 | Carrara et al. | 424/449 |
| 2007/0166361 A1 | 7/2007 | Carrara et al. | 424/448 |
| 2008/0227763 A1 | 9/2008 | Lanquetin et al. | 514/177 |

FOREIGN PATENT DOCUMENTS

| | | |
|---|---|---|
| EP | 0 250 125 B1 | 12/1987 |
| EP | 0 261 429 A1 | 3/1988 |
| EP | 0 267 617 A1 | 5/1988 |
| EP | 0 271 983 A1 | 6/1988 |
| EP | 0 279 977 A2 | 8/1988 |
| EP | 0 325 613 B1 | 6/1989 |
| EP | 0 367 431 A1 | 5/1990 |
| EP | 0 409 383 B1 | 1/1991 |
| EP | 0 435 200 B1 | 7/1991 |
| EP | 0 491 803 B1 | 7/1992 |
| EP | 0 526 561 B1 | 2/1993 |
| EP | 0 643 963 B1 | 3/1995 |
| EP | 0 655 900 B1 | 6/1995 |
| EP | 0 672 422 A1 | 9/1995 |
| EP | 0 719 538 B1 | 7/1996 |
| EP | 0 785 211 A1 | 7/1997 |
| EP | 0 785 212 A1 | 7/1997 |
| EP | 0 802 782 B1 | 10/1997 |
| EP | 0 804 926 B1 | 11/1997 |
| EP | 0 811 381 A1 | 12/1997 |
| EP | 0 814 776 B1 | 1/1998 |
| EP | 0 859 793 B1 | 8/1998 |
| EP | 0 868 187 B1 | 10/1998 |
| EP | 1 089 722 B1 | 4/2001 |
| EP | 1 323 430 A2 | 7/2003 |
| EP | 1 323 431 A2 | 7/2003 |
| EP | 1 325 752 A1 | 7/2003 |
| FR | 2 518 879 A1 | 7/1983 |
| FR | 2 776 191 A1 | 9/1999 |
| JP | 9-176049 A | 7/1997 |
| WO | WO 90/11064 A1 | 10/1990 |
| WO | WO 92/08730 A1 | 5/1992 |
| WO | WO 94/06437 A1 | 3/1994 |
| WO | WO 95/18603 A1 | 7/1995 |
| WO | WO 95/29678 | 11/1995 |
| WO | WO 95/29678 A1 | 11/1995 |
| WO | WO 97/03676 A1 | 2/1997 |
| WO | WO 97/29735 A1 | 8/1997 |
| WO | WO 97/34607 A1 | 9/1997 |
| WO | WO 98/17316 | 10/1997 |
| WO | WO 98/37879 A1 | 9/1998 |
| WO | WO 99/20257 A1 | 4/1999 |
| WO | WO 99/24041 A1 | 5/1999 |
| WO | WO 99/48477 A1 | 9/1999 |
| WO | WO 01/80796 | 11/2001 |
| WO | WO 02/11768 | 2/2002 |
| WO | WO 02/17967 A1 | 3/2002 |
| WO | WO 02/22132 A2 | 3/2002 |
| WO | WO 2004/037173 A2 | 5/2004 |
| WO | WO 2004/080413 * | 9/2004 |
| WO | WO 2004/080413 A2 | 9/2004 |
| WO | WO 2005/039531 A1 | 5/2005 |

OTHER PUBLICATIONS

Kotiyan et al., "Eudragits:Role as crystallization inhibitors in drug-in-adhesive transdermal systems of estradiol," European Journal of Pharmaceutics and Biopharmaceutics 52: 173-180 (2001).

Lipp, "Selection and use of crystallization inhibitors for matrix-type transdermal drug-delivery systems containing sex steroids," J. Pharm. Pharmacol. 50: 1343-1349 (1998).

Moser et al., "Passive skin penetration enhancement and its quantification in vitro," European Journal of Pharmaceutics and Biopharmaceutics 52: 103-112 (2001).

P. Mura et al., XP-002315954, "Evaluation of Transcutol as a Clonazepam Transdermal Permeation Enhancer From Hydrophilic Gel Formulations", European Journal of Pharmaceutical Sciences, vol. 9, pp. 365-372 (2000).

R. Panchagnula et al., "Development and evaluation of an intracutaneous depot formulation of corticosteroids using transcutol as a cosolvent: in-vitro, ex-vivo and in-vivo rat studies," J. Pharm. Pharmacol. 1991, 43: 609-614.

L. Pavliv et al., "Topical formulation development of a novel thymidylate synthase inhibitor for the treatment of psoriasis," International Journal of Pharmaceutics 1994, 105: 227-233.

W.A. Ritschel et al., "In vitro skin penetration of griseofulvin in rat and human skin from an ointment dosage form," Arzneimittelforschung. 1988, 38(11): 1630-1632.

W.A. Ritschel et al., "Use of sorption promoters to increase systemic absorption of coumarin from transdermal drug delivery systems," Arzneimittelforschung. 1988, 38(12): 1774-1777.

W.A. Ritschel et al., "Development of an intracutaneous depot for drugs," Skin Pharmacol. 1991, 4:235-245.

J. Rojas, "Optimization of binary and ternary solvent systems in the percutaneous absorption of morphine base," S.T.P. Pharma Sciences 1991, 1(1): 70-75.

E. Touitou, "Enhanced permeation of theophylline through the skin and its effect on fibroblast proliferation," International Journal of Pharmaceutics 1991, 70: 159-166.

A. Watkinson, "Aspects of the transdermal delivery of prostaglandins," International Journal of Pharmaceutics 1991, 74: 229 236.

M. Yazdanian et al., "The effect of diethylene glycol monoethyl ether as a vehicle for topical delivery of ivermectin," Veterinary Research Communications 1995, 19(4): 309-319.

English Abstract NLM2807923 XP-002337932 ,"Promoting Penetration of Locally Applied Substances by Urea".

P. Karande and S. Mitragotri, "High Throughput Screening of Transdermal Formulations," Pharmaceutical Research, 2002, 19(5): 655-660.

J. Fang et al., XP-0007999490, "Effect of Adhesive and Drug reservoir on in vitro transdermal delivery of Nocotine," Pharmazie, Die, Govi Verlag, Eschborn, De, (1999), 54(2): 154-155.

David W. Osborne et al., XP 002337808, "Skin Penetration Enhancers Cited in the Technical Literature".

A.C. Williams et al., XP 000645464,"Urea Analogues in Propylene Glycol as Penetration Enhancers in Human Skin", International Journal of Pharmaceutics, vol. 36, pp. 43-50 (1989).

Oxytrol Data Sheet.

Koichi Takahashi et al., "Effect of Vehicles on Diclofenac Permeation across Excised Rat Skin", Biol. Pharm. Bull., vol. 18, No. 4, pp. 571-575 (1995).

Budavari et al., The Merk Index, 1996, Merck Research Laboratories, 12th Edition, pp. 253 and 269.

"New Drug Application: Elestrin, estradiol, Treatment for Postmenopausal Symptoms. BioSante Pharmaceuticals Announces Bio-E-Gel NDA Submission," Internet article, [online], Feb. 16, 2006; retrieved from the Internet: URL:http://www.drugs.com/nda/elestrin__060216.html (retrieved on Sep. 18, 2007).

US 6,214,374, 04/2001, Schmirier et al. (withdrawn)

* cited by examiner

Figure 1 Mean Change From Baseline in Daily Moderate-to-Severe Hot Flash Rate (ITT-LOCF)

*Statistically significant difference from placebo (p<0.01, p<0.001, or p<0.0001) maintained through Week 12.

Figure 2  Mean Change From Baseline in Daily Hot Flash Severity (ITT-LOCF)

*Statistically significant difference from placebo (p<0.05, p<0.01, p<0.001, or p<0.0001) maintained through Week 12. Baseline hot flash severity was 2.4 in all treatment groups.

Figure 3

METHODS OF TREATING HOT FLASHES WITH FORMULATIONS FOR TRANSDERMAL OR TRANSMUCOSAL APPLICATION

This application claims the benefit of provisional application 60/794,015 filed Apr. 21, 2006, and the entire content is expressly incorporated herein by reference thereto.

FIELD OF INVENTION

The present invention relates generally a method for treating hot flashes by administering formulations for the transdermal or transmucosal delivery of estrogen. The formulations of the invention are effective at treating hot flashes at surprisingly low daily doses, preferably the lowest effective dose of estrogen that is effective at treating hot flashes. The preferred formulation comprises estrogen, an alcohol, a polyalcohol, and a permeation enhancer. Preferably, the formulation is substantially free of malodorous, and irritation causing long-chain fatty alcohols, long-chain fatty acids, and long-chain fatty esters, and delivers effective therapeutic levels of estrogen.

BACKGROUND ART

Transdermal and/or transmucosal delivery of active agents provide a convenient, pain-free, and non-invasive method of administering active agents to a subject. Additionally, the administration of active agents, such as drugs, through the skin or mucosal surface avoids the well-documented problems associated with the "first pass effect" encountered by oral administration of active agents. As known in the art, orally administered drugs are absorbed and enter the bloodstream where they are transported by the portal vein directly to the liver before entering the general circulation of the body. If the drug is subject to a high hepatic clearance, i.e., it is rapidly metabolized by the liver, then a substantial fraction of the absorbed dose is extracted from the blood and metabolized before it ever reaches the systemic circulation. A consequence of this "first pass effect" phenomenon is a significant reduction in the bioavailability of the drug. In some instances, the first pass effect is so large as to render oral administration of a drug ineffective. Furthermore, all the orally absorbed drug is concentrated in the portal vein producing a much higher concentration in portal blood than the corresponding systemic levels. In the case of steroidal hormones, including estrogens, the primary concern of the higher portal vein concentrations of the drug is a greater dose-dependant genomic effect on liver protein synthesis than the transdermal and transmucosal delivery systems. For a period of time, in the order of months, these very high hormone levels in the portal vein quickly and significantly stimulate the production of higher circulating levels of thrombogenic clotting protein factors and free fatty acids. This phenomenon is not seen to the same extent with transdermal administration as the hormone absorbed transdermally reaches the liver at the lower systemic hormone level eliminating this fast increase in protein and fatty acid production.

Although the transdermal and/or transmucosal delivery of active agents overcome some of the problems associated with oral administration of active agents, such as that described above, they are not free of their own drawbacks. Problematically, transdermal drug delivery systems are typically restricted to low-molecular weight drugs and those with structures having the proper lipophilic/hydrophilic balance. High molecular weight drugs, or drugs with too high or low hydrophilic balance, often cannot be incorporated into current transdermal systems in concentrations high enough to overcome their impermeability through the stratum corneum. Specifically, polar drugs tend to penetrate the skin too slowly, and since most drugs are of a polar nature, this limitation is significant.

Efforts have been made in the art to chemically modify the barrier properties of skin to permit the penetration of certain agents (since diffusion is primarily controlled through the stratum corneum), enhance the effectiveness of the agent being delivered, enhance delivery times, reduce the dosages delivered, reduce the side effects from various delivery methods, reduce patient reactions, and so forth.

In this regard, penetration enhancers have been used to increase the permeability of the dermal surface to drugs, and are often protons accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among others.

The penetration enhancers used and thought to be necessary to transdermally deliver active agents such as steroid hormones, namely, compounds such as long chain fatty acids such as oleic acids, fatty alcohols such as lauryl alcohol and long-chain fatty esters such as isopropyl myristate, tend to include aliphatic groups that make the formulations oily and malodorous.

For example, U.S. Pat. No. 5,891,462 teaches the use of lauryl alcohol as a permeation enhancer for estradiol and norethindrone acetate. Such formulations are not appealing to the user nor to anyone else in close proximity to the user. Although this particular patent discloses three examples of estradiol or norethindrone acetate formulations having no lauryl alcohol component, such formulations are comparative examples that are intended to illustrate the long held position that long chain fatty alcohols such as lauryl alcohol are necessary to transdermally deliver norethindrone acetate in combination with estradiol to a subject.

Additionally, for example, the known testosterone gel formulations FORTIGEL® and TOSTRELLE® (Cellegy Pharma, South San Francisco, Calif.), both include ethanol, propanol, propylene glycol, carbomer, triethanolamine, purified water, and oleic acid as a permeation enhancer, the latter being responsible for the irritating and malodorous characteristics of these formulations. Also, TESTIM® (Auxilium Pharmaceuticals, Norristown, Pa.) is a 1% testosterone gel and includes pentadecalactone, acrylates, glycerin, polyethylene glycol (PEG), and pentadecalactone as a permeation enhancer. It is a very odoriferous compound. Also, TESTIM® is not desirable because it contains undesirable amounts of glycerin which are not well tolerated by the skin.

Thus, there is a need for a transdermal formulation that adequately delivers active agents to patients with skin tolerability, but does not include the unpleasant odor common to the prior art formulations.

SUMMARY OF THE INVENTION

The present invention provides methods and compositions for treating hot flashes, by administering to a subject in need of such treatment a topical or transmucosal formulation, the formulation comprising an amount of estrogen which is effective at treating hot flashes, and a topically or transmucosally acceptable delivery vehicle. As demonstrated herein, the Applicants have found that the formulations are effective at treating hot flashes at surprisingly low daily dosages. In accordance with the invention, the amount of estrogen in the formulation is the lowest effective dose which is effective at treating hot flashes in a subject in need thereof. As used herein, the term "lowest effective dose" is the daily dose that is effective at treating hot flashes, under which there is no lower effective dose.

For example, it has unexpectedly been found that a 0.87 g daily dose of a formulation comprising 0.52 mg estrogen according to the invention that provides an estimated nominal daily estrogen dose of about 10 to about 15 micrograms, and a resulting serum level of estradiol of about 25 to about 50 pg/ml, is effective at treating hot flashes in subjects undergoing treatment. In one embodiment, this dose is the lowest effective dose of estrogen to treat hot flashes.

The formulation of the invention comprises estrogen in an amount from about 0.45 mg to about 0.6 mg; and a delivery vehicle, which may, in one embodiment, comprise a $C_2$ to $C_4$ alkanol, a polyalcohol, and a permeation enhancer of monoalkyl ether of diethylene glycol present in an amount sufficient to provide permeation enhancement of the active agent through mammalian dermal or mucosal surfaces.

In one embodiment, the formulation is administered in an amount of from about 0.75 g to about 1 g daily, preferably from about 0.85 g to about 0.9 g daily, and more preferably in an amount of about 0.87 g daily. In another embodiment, the formulation comprises from about 0.01% to about 10% by weight of estrogen. In a more preferred embodiment, the formulation comprises about 0.06% by weight of estrogen, corresponding to about 0.45 mg estrogen in a 0.75 g dose of the formulation, about 0.52 mg in a 0.87 g dose of the formulation, and about 0.6 mg estrogen in a 1 g dose of the formulation.

In one embodiment, the formulation provides an estimated nominal daily estrogen dose of from about 10 to about 15 micrograms, preferably from about 11 to about 14 micrograms, more preferably from about 12 to about 13 micrograms, and even more preferably an estimated nominal daily estrogen dose of about 12.5 micrograms.

In another embodiment, the amount of estrogen which is administered is effective to produce a resulting serum estradiol level of between about 25 pg/ml to about 50 pg/ml, preferably an amount of between about 30 pg/ml to about 40 pg/ml, and most preferably an amount about 34.4 pg/ml, in subjects receiving the formulation.

In one currently preferred embodiment, the formulation is administered in an amount of about 0.87 g daily, comprises about 0.06% by weight estrogen (corresponding to about 0.52 mg estrogen), the estimated nominal daily estrogen dose provided by the formulation is about 12.5 micrograms, and the resulting serum estradiol level is about 34.3 pg/ml.

Advantageously, the formulations are substantially free of long-chain fatty alcohols, long chain fatty acids and long-chain fatty esters, thus avoiding potential undesirable odor and irritation effects caused by such compounds during use of the formulation. Thus, advantageously, the formulations of the present invention do not include the undesirable-odor causing and irritation causing permeation enhancers that were once thought to be necessary for such transdermal or transmucosal formulations.

In accordance with the invention, the polyalcohol can be advantageously present in an amount between about 1% and 30% by weight of the vehicle. The monoalkyl ether of diethylene glycol can be present in an amount of about 0.2% and 25% by weight of the vehicle and the alkanol can be present in an amount between about 5 to 75% by weight of the vehicle. Generally, the alkanol can be present in a hydroalcoholic mixture with water.

The alkanol can be an ethanol, isopropanol, or n-propanol. Preferably, the alkanol is ethanol. The polyalcohol can be propylene glycol, butylene glycol, hexylene glycol, and ethylene glycol. Preferably, the polyalcohol is propylene glycol. The permeation enhancer of monoalkyl ether of diethylene is, for example, diethylene glycol monoethyl ether or diethylene glycol monomethyl ether. Preferably, the permeation enhancer is diethylene glycol monoethyl ether.

The estrogen can be present in any form known in the art, for example, 17 beta-estradiol, estradiol, estradiol benzoate, estradiol 17 beta-cypionate, estriol, estrone, ethinyl estradiol, mestranol, moxestrol, mytatrienediol, polyestradiol phosphate, quinestradiol, and quinestrol, or any combination thereof. Estradiol is the preferred estrogen.

The formulation can further include at least one of a gelling agent, neutralizing agent; buffering agent, moisturizing agent, humectant, surfactant, antioxidant, emollient, or buffer, and the like. The formulation can be applied in the form of a gel, lotion, cream, spray, aerosol, ointment, emulsion, suspension, liposomal system, lacquer, patch, bandage, or occlusive dressing and the like.

The formulations can be administered to male and female subjects suffering from hot flashes. In one embodiment the subject is a female, e.g., a postmenopausal woman. In another embodiment, the subject is a male. In another embodiment, the subject has an estrogen deficiency.

The invention also relates to a method of preparing a topical or transmucosal formulation for delivering the lowest effective dose of estrogen for treating hot flashes in a subject, and to the resultant compositions that are prepared. To prepare the formulation, a delivery vehicle is formed by mixing together a $C_2$ to $C_4$ alkanol, a polyalcohol, and a permeation enhancer of monoalkyl ether of diethylene glycol present in an amount sufficient to provide permeation enhancement of the active agent through dermal or mucosal surfaces; and then estrogen is provided or included in the delivery vehicle in an amount that provides a daily dosage of from about 0.45 mg to about 0.6 mg.

BRIEF DESCRIPTION OF THE DRAWINGS

The features and benefits of the invention will now become more clear from a review of the following detailed description of illustrative embodiments and the accompanying drawings, wherein.

DETAILED DESCRIPTION OF THE PREFERRED EMBODIMENTS

The present invention provides compositions and methods for treating hot flashes, by administering to a subject in need of such treatment a topical transdermal or transmucosal formulation, the formulation comprising an amount of estrogen which is effective at treating hot flashes, and a transdermally or transmucosally acceptable delivery vehicle. A preferred delivery vehicle comprises a $C_2$ to $C_4$ alkanol, a polyalcohol, and a permeation enhancer of monoalkyl ether of diethylene glycol present in an amount sufficient to provide permeation enhancement of the active agent through mammalian dermal or mucosal surfaces.

As demonstrated herein, the Applicants have found that the formulations of the present invention are effective at treating hot flashes at unexpectedly low doses. In accordance with the invention, the amount of estrogen which is administered is from about 0.45 mg to about 0.6 mg daily, preferably about 0.52 mg daily. The amount of estrogen is, in one embodiment, the lowest effective dose which is effective at treating hot flashes in a subject in need thereof.

The formulation can comprise from about 0.01% to about 10% by weight of estrogen. In one embodiment, the formulation comprises from about 0.01% to about 5% by weight of estrogen. In another embodiment, the formulation comprises from about 0.01% to about 1% by weight of estrogen. In another embodiment, the formulation comprises from about 0.01% to about 0.5% by weight of estrogen. In another embodiment, the formulation comprises from about 0.01% to about 0.1% by weight of estrogen. In a currently preferred embodiment, the formulation comprises about 0.06% by weight of estrogen.

The formulations of the invention can be administered in any amount that is determined safe and effective at treating hot flashes, and preferably contain estrogen at the lowest effective dose to treat hot flashes in a subject undergoing treatment. The estrogen dose will, of course, depend on a variety of factors such as the weight, age, sex, body fat and rate of metabolism of the subject being treated, and can be determined by a person of skill in the art. In one embodiment, the estrogen dose is from about 0.45 mg to about 0.6 mg, preferably from about 0.5 mg to about 0.55 mg, more preferably about 0.52 mg.

Typical total amount of the formulation (i.e., estrogen and delivery vehicle) to be administered range from about 0.1 g to about 10 g daily. In one embodiment, the formulation is administered in an amount of from about 0.25 g to about 5 g daily. In another embodiment, the formulation is administered in an amount of from about 0.75 g to about 1 g daily. In yet another embodiment, the formulation is administered in an amount of from about 0.85 g to about 0.9 g daily. In a currently preferred embodiment, the formulation is administered in an amount of about 0.87 g daily.

In one embodiment, the amount of estrogen which is administered produces a resulting serum estradiol level of between about 25 pg/ml to about 50 pg/ml or less in a subject receiving the formulation. In another embodiment, the amount of estrogen which is administered is effective to produce a resulting serum estradiol level of between about 30 pg/ml to about 40 pg/ml or less. In yet another embodiment, the amount of estrogen which is administered is effective to produce a resulting serum estradiol level of about 34.3 pg/ml or less. As demonstrated herein, these low daily dose levels have unexpectedly been found to be effective at treating hot flashes.

In one embodiment, the formulation provides an estimated nominal daily estrogen dose of from about 10 to about 15 micrograms in a subject receiving the formulation. In another embodiment, the formulation provides an estimated nominal daily estrogen dose of from about 11 to about 14 micrograms. In another embodiment, the formulation provides an estimated nominal daily estrogen dose of from about 12 to about 13 micrograms. In a currently preferred embodiment, the formulation provides an estimated nominal daily estrogen dose of about 12.5 micrograms.

In one currently preferred embodiment, the formulation is administered in an amount of about 0.87 g daily, the estimated nominal daily estrogen dose provided by the formulation is about 12.5 micrograms, and the resulting serum estradiol level is about 34.3 pg/ml. The formulation of the preferred embodiment comprises about 0.06% by weight estrogen, corresponding to about 0.52 mg estrogen per 0.87 g of the formulation.

As used herein, the term "treating" includes ameliorating, preventing, suppressing, inhibiting or reducing the incidence of, or alleviating the symptoms or severity of hot flashes.

The formulations of the present invention can be clear, water washable, cool to the touch, quick drying, spreadable and/or a non-greasy formulations, such as a gel. In other aspects of the invention, the formulation can be a spray, ointment, aerosol, patch, buccal and sublingual tablets, suppositories, vaginal dosage form, or other passive or active transdermal devices for absorption through the skin or mucosal surface. The formulations of the present invention can be applied directly to the skin such as by, for example and not limitation, a gel, ointment, or cream or indirectly though a patch, bandage, or other occlusive dressing.

Advantageously, the substantial omission of the long chain fatty alcohols, long-chain fatty acids, and long-chain fatty esters provides a formulation that does not have the unpleasant odor, irritation, and/or greasy texture caused by formulations of the prior art that include one or more of such compounds. Thus, the formulation in accordance with the present invention will result in greater patient compliance. In one embodiment, the formulations are substantially free of such alcohols, fatty acids, and long-chain fatty esters so that the odors associated with those compounds do not emanate from the formulation. In this regard, "substantially free" means an amount which does not impart a perceptible odor to the formulation at a distance of 1 meter or less, preferably an amount which does not impart a perceptible odor to a subject receiving the formulation. Such formulations are also deemed to be substantially odor free, except for the odor of ethanol, which evaporates quickly after application. For the purpose of example and illustration, a formulation comprising fatty alcohols, fatty acids and/or fatty esters in an amount of less than about 0.04% by weight of the formulation is substantially odor free.

The present invention relates generally to formulations for providing active agent, e.g., estrogen, to subjects. The formulations are effective at treating hot flashes at surprisingly low doses of estradiol in subjects receiving the formulation. In one preferred embodiment, the invention further relates to formulations for the transdermal or transmucosal administration of estrogen, that are substantially free of malodorous, and irritation causing long-chain fatty alcohols, long-chain fatty acids, and long-chain fatty esters. Surprisingly, the formulation of the present invention can achieve sufficient absorption to result in an effective dosage of the active agent circulating in serum without the inclusion of the long-chain fatty alcohols, the long-chain fatty acids and the long-chain fatty esters that have been used to date.

The delivery vehicle of the present invention preferably comprises a $C_2$ to $C_4$ alkanol, a polyalcohol, and a permeation enhancer of monoalkyl ether of diethylene glycol in an amount sufficient to provide permeation enhancement of the active agent through mammalian dermal or mucosal surfaces.

In accordance with the invention, the polyalcohol is advantageously present in an amount between about 1% and 30% by weight of the vehicle, preferably from 3% to 20% by weight and more preferably from about 4% to 10% by weight. The monoalkyl ether of diethylene glycol is present in an amount of about 0.2% and 25% by weight, preferably between about 1% to 15% by weight and more preferably between about 2% to 8% by weight. The alkanol is present in an amount between about 5 to 75% by weight, preferably between about 15% to 65% by weight, and more preferably between about 20% and 55% by weight. The alkanol can be present in a hydroalcoholic mixture with water. The mixture is present in an amount between about 40% and 98% by weight of the delivery vehicle, with the alcohol being present in an amount between about 5% to 80% by weight of the hydroalcoholic mixture, and the water present in an amount between about 20% to 95% by weight of the hydroalcoholic mixture. Preferably, the alcohol is present in an amount of about 40 to 60% by weight, preferably about 46% by weight and the water in an amount of 40 to 50% by weight, preferably about 41% by weight of the hydroalcoholic mixture.

For example, the monoalkyl ether of diethylene glycol is diethylene glycol monomethyl ether or diethylene glycol monoethyl ether or mixtures thereof. Also for example, the polyalcohol is propylene glycol, dipropylene glycol or mixtures thereof. The polyalcohol and the permeation enhancer can be in present in a weight ratio of about 2:1 to 1:1. Alternatively, the polyalcohol and permeation enhancer can be present in a weight ratio of about 1.25:1 to 1.2 to 1.

For the purpose of illustration and not limitation, the alkanol can be a $C_2$ to $C_4$ alcohol such as ethanol, isopropanol, or n-propanol. The alkanol is preferably ethanol. As known in the art, the amount of the alcoholic component of the formulation can be selected to maximize the diffusion of the active agent through the skin while minimizing any negative impact on the active agent itself or desirable properties of the formulation.

Examples of estrogens which can be useful in this invention include estrogens such as 17 beta-estradiol, estradiol, estradiol benzoate, estradiol 17 beta-cypionate, estriol, estrone, ethinyl estradiol, mestranol, moxestrol, mytatrienediol, polyestradiol phosphate, quinestradiol, and quinestrol, or any combination thereof.

The formulation may further include a thickening agent or gelling agent present in an amount sufficient to alter the viscosity of the formulation. A gelling agent can be selected from the group including: carbomer, carboxyethylene or polyacrylic acid such as Carbopol 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, Methocel grades; natural gums such as arabic, xanthan, guar gums, alginates; polyvinylpyrrolidone derivatives such as Kollidon grades; polyoxyethylene polyoxypropylene copolymers such as Lutrol F grades 68, 127. Other gelling agents include chitosan, polyvinyl alcohols, pectins, veegum grades. A tertiary amine, such as triethanolamine or trolamine, can be included to thicken and neutralize the system.

A polymer or copolymer of acrylic acid, such as a carbomer acts as a gelling forming and facilitates the release of lipophilic active agent and penetration enhancer. Preferably, the gelling agent is Lutrol F grades and Carbopol grades. The gelling agent is present from about 0.2 to about 30.0% by weight of the formulation depending on the type of polymer. For example, the gelling agent is preferably present in an amount between about 0.5% to 2% by weight for polyacrylic acids, and between about 1 to 5% by weight for celluloses.

The amount and the type of the gelling agent in the formulation can be selected to provide the desired product consistency and/or viscosity to facilitate application to the skin.

Preservatives. The formulation may further include preservatives such as, but not limited to, benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10.0% by weight depending on the type of compound.

Antioxidant. The formulation may optionally include antioxidants such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0% by weight of the formulation depending on the type of compound.

Buffers. The formulation may further include buffers such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art can be included. The buffer may replace up to 100% of the water amount within the formulation.

Humectant. The formulation may further include humectant, such as but not limited to glycerin, propylene, glycol, sorbitol, triacetin. The humectant is present from about 1 to 10.0% by weight of the formulation depending on the type of compound.

Sequestering agent. The formulation may further include a sequestering agent such as edetic acid. The sequestering agent is present from about 0.001 to about 5.0% by weight of the formulation depending on the type of compound.

Surfactant. The formulation may further include anionic, non-ionic or cationic surfactants. The surfactant is present from about 0.1% to about 30.0% by weight of the formulation depending on the type of compound.

pH regulator. Optionally, the formulation may include a pH regulator, generally, a neutralizing agent, which can optionally have crosslinking function. By way of example and not limitation, the pH regulator may include a ternary amine such as triethanolamine, tromethamine, tetrahydroxypropylethylendiamine, NaOH solution. The pH regulator is present in the formulations in about 0.05 to about 2.0% by weight.

Moisturizers and Emollients. Optionally, the formulation may include moisturizers and/or emollients to soften and smooth the skin or to hold and retain moisture. By way of example and not limitation, moisturizers and emollients may include cholesterol, lecithin, light mineral oil, petrolatum, and urea.

For any particular formulation, the active agent and other ingredients can be selected to achieve the desired drug delivery profile and the amount of penetration desired. The optimum pH may also be determined and may depend on, for example, the nature of the hormone, the base, and degree of flux required.

In certain preferred embodiments of the present invention, the formulation may have the following formula.

TABLE 1

| | |
|---|---|
| Estradiol | 0.01%-2% |
| Carbomer | 0.05%-4% |
| Triethanolamine (adjust to pH 5.9) | 0.05%-1% |
| Alcohol | 20%-65% |
| Propylene glycol | 1%-15% |
| Diethylene glycol monoethyl ether | 1%-15% |
| Ion Exchange Purified Water q. ad. | 20%-65% |

TABLE 2

| | |
|---|---|
| Estradiol | 0.01%-1% |
| Carbomer 940 | 1.2% |
| Triethanolamine (adjust to pH 5.9) | 0.4% |
| Alcohol | 46.28% |
| Propylene glycol | 6% |
| Diethylene glycol monoethyl ether | 5% |
| Disodium EDTA | 0.06% |
| Ion Exchange Purified Water q. ad. | 100% |

TABLE 3

| | |
|---|---|
| Estradiol | 0.06% |
| Ethanol, Dehydrated | 46.28% |
| Propylene Glycol | 6% |
| Diethylene glycol monoethyl ether (Transcutol ® P) | 5% |
| Carbopol ® 980 (Carbomer 940) | 1.20% |
| Triethanolamine (Trolamine 99) | 0.35% |

The formulations of the present invention are advantageous at least for the following reasons. First, the surprisingly low doses of the formulations give rise to serum levels of estradiol that are effective at treating hot flashes. For example, it has unexpectedly been found that about 0.87 g of the formulation comprising about 0.52 mg estrogen provides an estimated nominal daily estrogen dose of about 12.5 micrograms, and a resulting serum estradiol level of about 34.3 pg/ml. Surprisingly, this dose has been determined as the lowest effective dose to treat hot flashes. Advantageously, the formulation is safe and is associated with reduced side effects and risks compared to higher doses previously used.

Second, the formulations of the present invention are, in one embodiment, substantially free of long-chain fatty alcohols, long-chain fatty acids, and long-chain fatty esters. Surprisingly, the formulations exhibit skin penetration sufficient to deliver an effective dosage of the desired active agent(s) to the user. This is an unexpected advantage that those of ordinary skill in the art would not have readily discovered since it had been generally understood that long-chain fatty alcohols, long-chain fatty acids, and long chain fatty esters would be required to enhance skin penetration to permit an effective dose of an active agent to penetrate the skin.

Third, because the formulations preferably do not include aliphatic acid groups, such as fatty acids, that are commonly included in topical gels or lotions, they do not have the odor or oily texture which is associated with that ingredient as in presently-available gels or lotions.

Fourth, the absence of long-chain fatty alcohols, long-chain fatty acids, and long-chain fatty esters means that the irritation potential is lower and that there is less chance for the components to interact, reducing the need for antioxidants or preservatives in the formulations. Numerous studies acknowledge the irritation causing potential of unsaturated fatty acids such as oleic acid. See, Tanojo H. Boelsma E, Junginger H E, Ponec M, Bodde H E, "In vivo human skin barrier modulation by topical application of fatty acids," *Skin Pharmacol Appl. Skin Physiol.* 1998 March-April; 11 (2) 87-97. It is to be understood, however, that if such preservatives are desired, the invention encompasses formulations which include antioxidants or preservatives. The reduction in the number of ingredients is advantageous at least in reducing manufacturing costs, possible skin irritation and transfer to others. Additionally, the reduced number of ingredients increases the storage stability of the formulation by decreasing the chance that the ingredients will interact prior to being delivered. This does not, however, imply that additional ingredients cannot be included in the formulation for particular aesthetic and/or functional effects. For example, the formulations may optionally include one or more moisturizers for hydrating the skin or emollients for softening and smoothing the skin. Glycerin is an example of such a suitable moisturizing additive.

The formulations of the invention can be applied once daily, or multiple times per day depending upon the condition of the patient. The formulation of the invention can be applied topically to any body part, such as the thigh, abdomen, shoulder, and upper arm.

The invention includes the use of the formulations described above to treat subjects to increase circulating levels of active agents within the patient.

Preferred dosage units are capable of delivering an effective amount of the active agent over a period of about 24 hours. By an "effective" or "therapeutically effective" amount of an active agent is meant a nontoxic, but sufficient amount of the agent to provide the desired effect. The minimum or lowest effective dose of each active agent is of course preferred to minimize the side effects associated treatment with the selected active agent(s). The formulation is preferably applied on a regularly timed basis so that administration of the active agents is substantially continuous.

EXAMPLES

The following examples are illustrative and should not be interpreted as limiting.

Example 1

Study of the Safety and Efficacy of Topical Bio-E Gel® for Treatment of Vasomotor Symptoms and Vulvovaginal Atrophy Symptoms in Postmenopausal Females The objectives of this study were to evaluate the safety and efficacy of Bio-E Gel® 0.87 g, 1.7 g and 2.6 g (containing, respectively, 0.52 mg, 1.02 mg, and 1.56 mg estradiol), administered as a daily regimen, compared to that of placebo gel in the treatment of vasomotor symptoms and vulvovaginal atrophy symptoms in postmenopausal women. Eligible subjects were health post-menopausal women, with an estradiol serum concentration of ≦2.0 ng/dL, a follicle stimulating hormone (FSH) serum concentration of >40 mIU/mL, who exhibited ≧60 moderate-to-severe hot flashes each week during the first 2 weeks of screening.

Bio-E Gel® consisted of 0.06% estradiol in a hydroalcoholic gel formulation supplied in a metered-dose bottle that delivered 0.87 g (0.52 mg estrogen) Bio-E Gel®, 1.7 g (1.02 mg estrogen) Bio-E Gel®, or 2.6 g (1.56 mg estrogen) Bio-E Gel® per application. Daily topical application of Bio-E Gel® was administered by the subject on the upper arm/shoulder areas.

The parameters evaluated included hot flash rate and severity, vaginal atrophy assessments, adverse effects, safety laboratory tests, vitals, signs, weight, physical and gynecological examinations including endometrial biopsies and breast examinations, and skin irritation.

Results

Vasomotor Symptoms (Primary)

Figure 1:
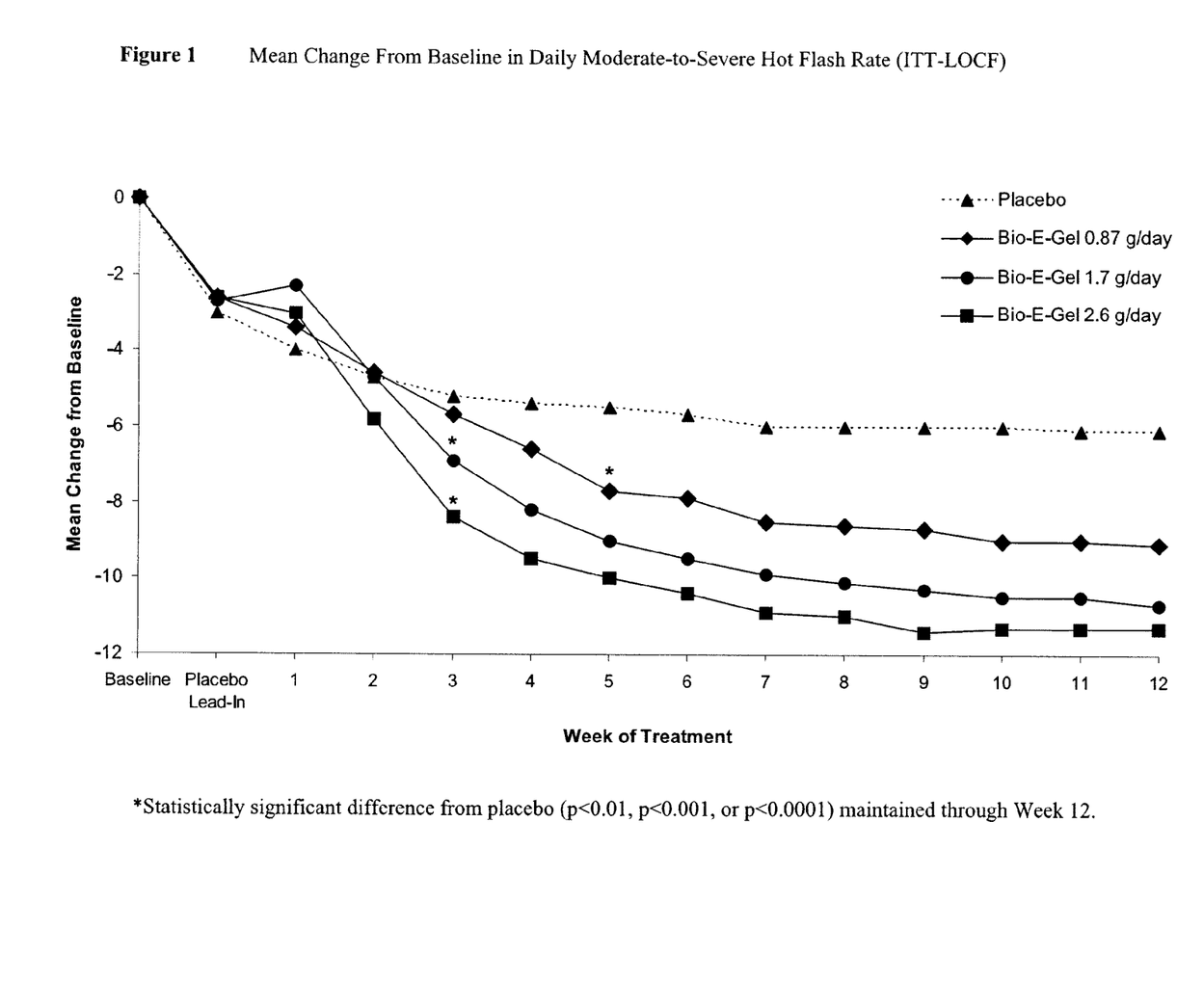
FIG. 1 is a graph depicting mean change from baseline in daily moderate-to-severe hot flash rate following administration of Bio-E Gel® 0.87 g/day (♦), 1.7 g/day (●), 2.6 g/day (■), and placebo (▲).

1) Mean Change from Baseline in Daily Moderate-to-Severe Hot Flash Rates Over Time As demonstrated in FIG. 1 and Table 4, at the Week 4 primary endpoint, each treatment group showed a reduction from baseline in daily moderate-to-severe hot flash rate, and the change was statistically significantly greater for subjects receiving 1.7 g/day Bio-E Gel® and 2.6 g/day Bio-E Gel® than for placebo (−8.2 and −9.5, respectively, vs. −5.4; p<0.0001 for both comparisons). In addition, the difference between these Bio-E Gel® groups and the placebo group in their number of hot flashes per day was >2.0, demonstrating that the reduction was also clinically meaningful. For subjects receiving 0.87 g/day Bio-E-Gel® the change from baseline in daily moderate-to-severe hot flash rate approached statistical significance difference at Week 4 (−6.6 vs. −5.4; p=0.0965). However, both a clinically and statistically significant difference from placebo was observed beginning at Week 5, indicating that 0.87 g/day is the lowest effective dose of Bio-E Gel® for the reduction of moderate-to-severe hot flashes.

At the Week 12 primary endpoint, the change from baseline in daily moderate-to-severe in hot flash rate was statistically and clinically significant for subjects receiving 0.87 g/day Bio-E gel, 1.7 g/day Bio-E Gel® and 2.6 g/day Bio-E Gel® compared to placebo (−9.1, −10.7, and −11.3, respectively, vs. −6.1; p<0.0001 for both comparisons) (Table 4 and FIG. 1).

TABLE 4

Mean Change From Baseline in Daily Moderate-to-Severe Hot flash Rate (ITT-LOCF)

| | Mean Change From Baseline[a] | | | |
|---|---|---|---|---|
| Evaluation | Placebo (N = 137) | Bio-E gel 0.87 g/day (N = 136) | Bio-E gel 1.7 g/day (N = 142) | Bio-E gel 2.6 g/day (N = 69) |
| Baseline (Mean ± SD)[b] | 13.5 ± 4.5 | 13.3 ± 4.6 | 13.1 ± 6.5 | 12.9 ± 4.5 |
| Placebo Lead-in | −3.0 | −2.6 | −2.7 | −2.6 |
| Week 1 | −4.0 | −3.4 | −2.3* | −3.0 |
| Week 2 | −4.7 | −4.6 | −4.7 | −5.8 |
| Week 3 | −5.2 | −5.7 | −6.9* | −8.4*** |
| Week 4 | −5.4 | −6.6 | −8.2*** | −9.5*** |
| Week 5 | −5.5 | −7.7** | −9.0*** | −10.0*** |
| Week 6 | −5.7 | −7.9** | −9.5*** | −10.4*** |
| Week 7 | −6.0 | −8.5*** | −9.9*** | −10.9*** |
| Week 8 | −6.0 | −8.6*** | −10.1*** | −11.0*** |
| Week 9 | −6.0 | −8.7*** | −10.3*** | −11.4*** |
| Week 10 | −6.0 | −9.0*** | −10.5*** | −11.3*** |
| Week 11 | −6.1 | −9.0*** | −10.5*** | −11.3*** |
| Week 12 | −6.1 | −9.1*** | −10.7*** | −11.3*** |

[a]Differences from baseline to each week based on LS means derived from the ANCOVA model with factors for baseline, treatment, site, and treatment-by-baseline interaction.
[b]Unadjusted means and standard deviations. Baseline based on the first 14 days of the Screening Period.
*P < 0.01,
**P < 0.001,
***P < 0.0001 for treatment comparison with placebo (Dunnett's test).

2) Mean Change From Baseline in Daily Hot Flash Severity Over Time

As demonstrated in Table 5, at the Week 4 primary endpoint, the reduction from baseline in daily hot flash severity was statistically significantly greater for subjects receiving 1.7 g/day Bio-E Gel® and 2.6 g/day Bio-E Gel® than for placebo (−0.7 and −1.0, respectively, vs. −0.3; p<0.0001 for both comparisons). On average, these reductions placed subjects in the Bio-E Gel® groups in the category of having mild-to-moderate hot flash severity, while those in the placebo group were still in the moderate-to-severe category. The change for subjects receiving 0.87 g/day Bio-E Gel® approached statistical significance from placebo (−0.5 vs. −0.3; p=0.0714) at week 4. However, both a clinically (mild-to-moderate vs. moderate-to-severe) and a statistically significant (−0.6 vs. −0.3; p=0.0083) difference from placebo was observed for this dose group beginning at Week 5.

At the Week 12 primary endpoint, the change from baseline in daily hot flash severity was statistically significantly greater for subjects receiving 0.87 g/day Bio-E gel, 1.7 g/day Bio-E Gel® and 2.6 g/day Bio-E Gel® than for placebo (−0.9, −1.4 and −1.6, respectively, vs. −0.4; p<0.001 for all comparisons) (Table 5).

Figure 2:
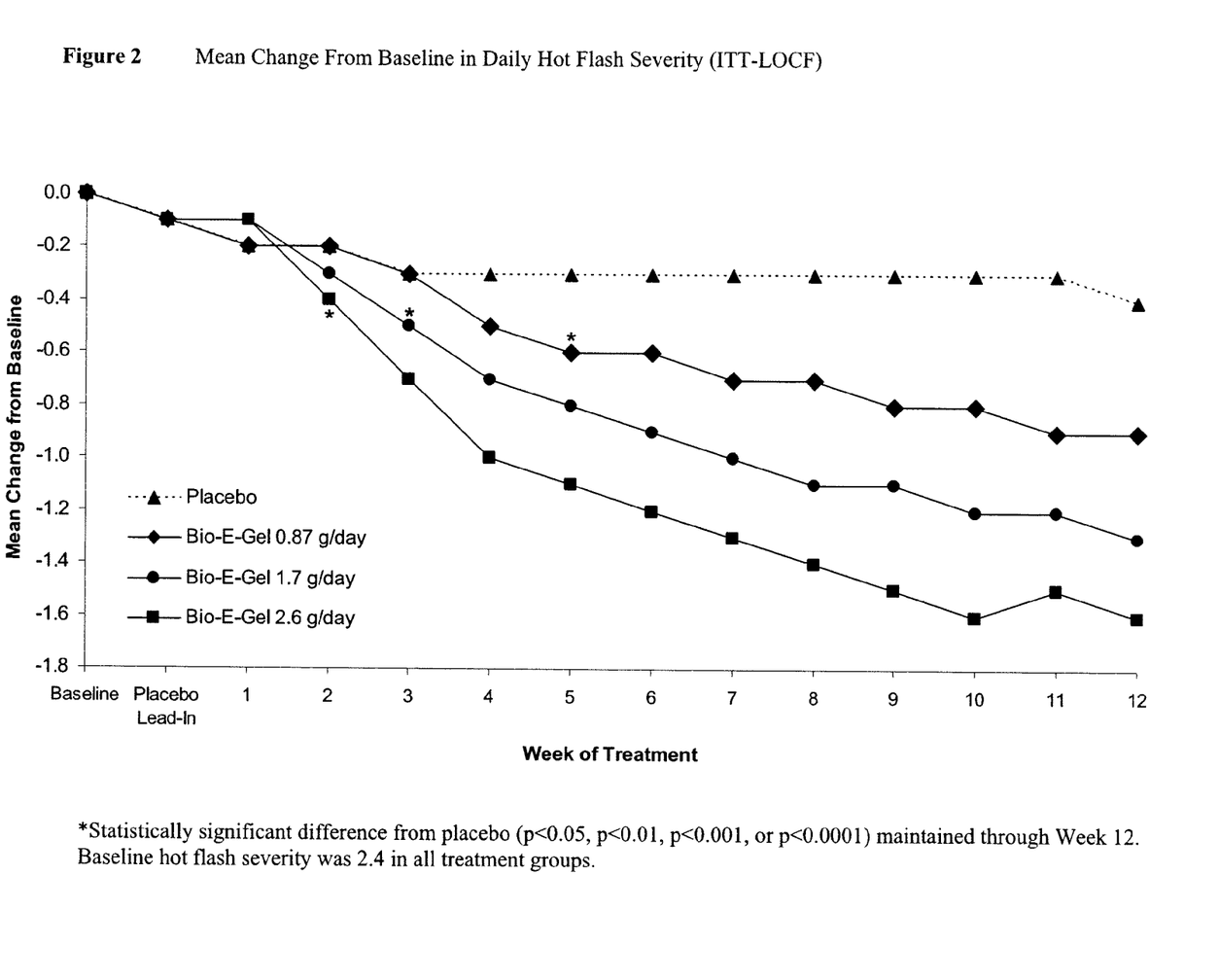
FIG. 2 is a graph depicting mean change from baseline in daily hot flash severity following administration of Bio-E Gel® 0.87 g/day (♦), 1.7 g/day (●), 2.6 g/day (■), and placebo (▲).

As illustrated in FIG. 2, the reduction from baseline in daily hot flash severity among subjects receiving Bio-E Gel® was dose-dependent, with progressively greater effects shown with increasing doses of Bio-E Gel® at each time point studied. In addition, the magnitude of reduction in hot flash severity was dose- and time-dependent. Similarly, the onset of severity reduction was dose-dependent, occurring somewhat later for subjects receiving 0.87 g/day Bio-E Gel® than for those receiving 2.6 g/day or 1.7 g/day. Significant differences from placebo in mean change from baseline in hot flash severity were noted at Week 5 for subjects receiving 0.87 g/day Bio-E Gel® (−0.6 vs. −0.3; p=0.0083), at Week 3 for subjects receiving 1.7 g/day (−0.5 vs. −0.3; p=0.0031), and at Week 2 for subjects receiving 2.6 g/day (−0.4 vs. −0.2; p=0.0210) (Table 5).

TABLE 5

Mean Change From Baseline in Daily Hot flash Severity (ITT-LOCF)

| | Mean Change From Baseline[a,b] | | | |
|---|---|---|---|---|
| Evaluation | Placebo (N = 137) | Bio-E gel 0.87 g/day (N = 136) | Bio-E gel 1.7 g/day (N = 142) | Bio-E gel 2.6 g/day (N = 69) |
| Baseline (Mean ± SD)[c] | 2.4 ± 0.3 | 2.4 ± 0.3 | 2.4 ± 0.3 | 2.4 ± 0.3 |
| Placebo Lead-in | −0.1 | −0.1 | −0.1 | −0.1 |
| Week 1 | −0.2 | −0.2 | −0.1 | −0.1 |
| Week 2 | −0.2 | −0.2 | −0.3 | −0.4† |
| Week 3 | −0.3 | −0.3 | −0.5* | −0.7*** |
| Week 4 | −0.3 | −0.5 | −0.7*** | −1.0*** |
| Week 5 | −0.3 | −0.6* | −0.8*** | −1.1*** |
| Week 6 | −0.3 | −0.6* | −0.9*** | −1.2*** |
| Week 7 | −0.3 | −0.7* | −1.0*** | −1.3*** |
| Week 8 | −0.3 | −0.7** | −1.1*** | −1.4*** |
| Week 9 | −0.3 | −0.8** | −1.1*** | −1.5*** |
| Week 10 | −0.3 | −0.8*** | −1.2*** | −1.6*** |
| Week 11 | −0.3 | −0.9*** | −1.2*** | −1.5*** |
| Week 12 | −0.4 | −0.9*** | −1.3*** | −1.6*** |

[a]Differences from baseline to each week based on LS means derived from the ANCOVA model with factors for baseline, treatment, and site.
[b]Severity score: 0 = none, 1 = mild, 2 = moderate, 3 = severe.
[c]Unadjusted means and standard deviations. Baseline based on the first 14 days of the Screening Period.
†P < 0.05,
*P < 0.01,
**P < 0.001,
***P < 0.0001 for treatment comparison with placebo (Dunnett's test).

Vulvovaginal Atrophy Symptoms (Primary)

1. Mean Change From Baseline in Most Bothersome Moderate-to-Severe Symptom (Week 12/Last Visit)

The mean change from baseline to Week 12 (or last visit for subjects who discontinued prematurely) in subjects' most bothersome moderate-to-severe vulvovaginal atrophy symptom is presented in Table 6. Approximately half of the subjects in each treatment group identified a most bothersome symptom at baseline that was moderate or severe for inclusion in this analysis. The mean baseline severity of the most bothersome moderate-to-severe vulvovaginal atrophy symptom ranged from 2.23 to 2.48 across treatment groups. At the Week 12 primary endpoint, a clinically meaningful reduction from baseline in severity of most bothersome vaginal atrophy symptom was observed among subjects receiving active treatment with Bio-E Gel®. Specifically, the average reduction from baseline among subjects receiving 0.87 g/day, 1.7 g/day, and 2.6 g/day Bio-E Gel® (−1.74, −1.53, and −1.75, respectively) placed the average severity in the range of none to mild, while among those receiving placebo, the reduction (−1.31) placed the average severity in the range of mild to moderate. A statistically significant difference from placebo was observed only in the 0.87 g/day Bio-E Gel® group (−1.74 vs. −1.31; p=0.0183), which had the largest sample size (N=67) for Week 12 data (Table 6). The smaller sample sizes in the higher dose Bio-E Gel® treatment groups may explain the lack of significance in these groups in comparison to placebo treatment, although the 2.6 g/day group approached statistical significance (p=0.0518).

2. Mean Change from Baseline in Vaginal pH (Week 12/Last Visit)

The mean change from baseline to Week 12 (or last visit for subjects who discontinued prematurely) in vaginal pH among subjects who had a vaginal pH>5.0 at baseline is presented in Table 6). The mean vaginal pH at baseline ranged from 6.07 to 6.31 across treatment groups. Relative to placebo, all Bio-E Gel® treatment groups showed a more acidic vaginal pH at Week 12, with the mean change from baseline in vaginal pH being −1.21, −1.20, and −1.31 in the 0.87 g/day, 1.7 g/day, and 2.6 g/day Bio-E Gel® groups. All reductions were statistically significantly (p<0.0001) greater relative to placebo (−0.17).

3. Mean Change from Baseline in Vaginal Maturation Index (VMI) (Week 12/Last Visit)

The VMI among subjects who had ≦5% superficial cells in the vaginal wall specimen at baseline is presented in Table 6. The mean VMI at baseline was similar across treatment groups, ranging from 40.6 to 42.3, and increased (i.e., decreased parabasal cells and increased superficial cells) substantially at Week 12 in all subjects receiving Bio-E gel. While the change in VMI was a score of 1.2 at Week 12 for placebo, the mean increase in VMI was approximately 18 in subjects receiving 0.87 g/day Bio-E gel, 26 in subjects receiving 1.7 g/day, and 28 in subjects receiving 2.6 g/day (p<0.0001 for all Bio-E Gel® groups) (Table 6).

TABLE 6

Mean Change From Baseline[a] in Most Bothersome Moderate-to-Severe Vulvovaginal Atrophy Symptom, Vaginal pH, and Vaginal Maturation Index (ITT-Observed Data)

| Evaluation | Mean Change From Baseline | | | |
|---|---|---|---|---|
|  | Placebo | Bio-E gel 0.87 g/day | Bio-E gel 1.7 g/day | Bio-E gel 2.6 g/day |
| Most bothersome moderate-to-severe vulvovaginal atrophy symptom[a,b] | | | | |
| N (Baseline/Week 12) | 64/62 | 69/67 | 64/61 | 35/35 |
| Baseline (Mean ± SD)[c] | 2.48 ± 0.50 | 2.36 ± 0.48 | 2.23 ± 0.43 | 2.26 ± 0.44 |
| Week 12 (last visit)[d] | −1.31 | −1.74[†] | −1.53 | −1.75 |
| Vaginal pH[e,f] | | | | |
| N (Baseline/Week 12) | 84/81 | 68/66 | 80/78 | 36/34 |
| Baseline (Mean ± SD)[c] | 6.28 ± 0.71 | 6.31 ± 0.62 | 6.18 ± 0.61 | 6.07 ± 0.62 |
| Week 12 (last visit)[d] | −0.17 | −1.21*** | −1.20*** | −1.31*** |
| Vaginal maturation index[e,g] | | | | |
| N (Baseline/Week 12) | 123/117 | 119/116 | 117/115 | 57/56 |
| Baseline (Mean ± SD)[c] | 40.6 ± 11.9 | 40.8 ± 12.8 | 41.5 ± 10.5 | 42.3 ± 10.8 |
| Week 12 (last visit)[d] | 1.2 | 17.9*** | 25.9*** | 28.3*** |

[a]Differences from baseline to Week 12 (last visit) based on LS means derived from the ANCOVA model with factors for baseline, treatment, and site.
[b]Based on subject rating of severity (0 = none, 1 = mild, 2 = moderate, 3 = severe) of 5 symptoms of vulvovaginal atrophy (dryness, irritation, pain passing urine, pain with sexual activity, bleeding with sexual activity) on the Vaginal Health Self-Assessment Questionnaire. Only those subjects who identified at least 1 moderate-to-severe symptom that was most bothersome to her are included in the analyses.
[c]Unadjusted means and standard deviations. Baseline based on the Visit 1 (Day -21) assessment.
[d]Assessments were made at Week 12 or at last visit for subjects who discontinued prematurely.
[e]Differences from baseline to Week 12 (last visit) based on LS means derived from the ANCOVA model with factors for baseline, treatment, site, and treatment-by-baseline interaction.
[f]Only those subjects who had vaginal pH >5.0 at baseline are included in the analyses.
[g]Only those subjects who had ≦5% superficial cells in the vaginal wall specimen at baseline are included in the analyses.
[†]P < 0.05,
***P < 0.0001 for treatment comparison with placebo (Dunnett's test).

Figure 3:
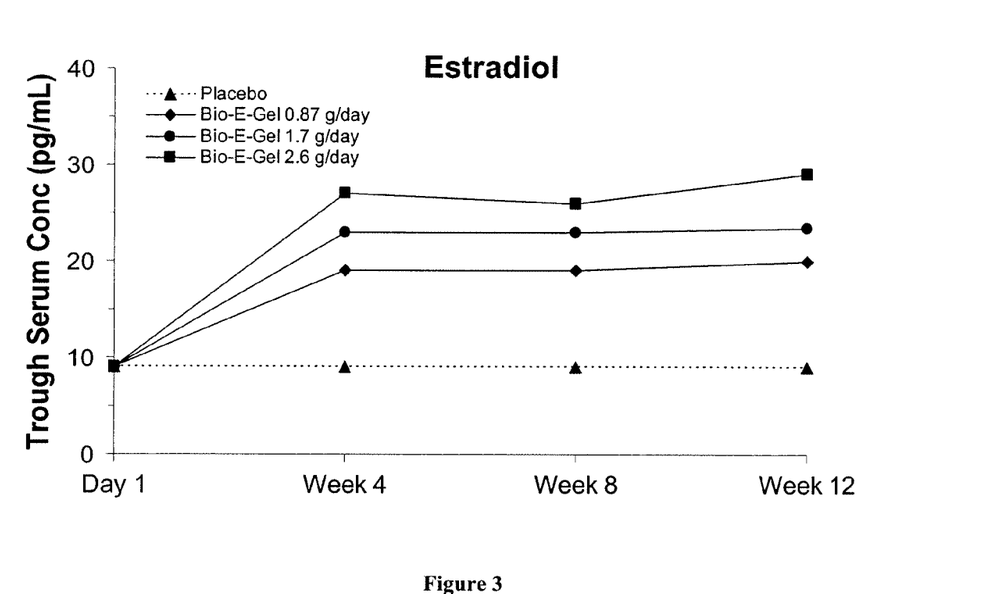
FIG. 3 is a graph depicting median trough concentrations of Bio-E Gel® over time following repeated administration of Bio-E gel 0.87 g/day (♦), 1.7 g/day (●), 2.6 g/day (■), and placebo (▲).

Mean, median, and range of trough serum concentrations of estradiol, at entry into the Double-Blind Treatment Period (Day 1) and at Week 4, Week 8, and Week 12 of the Double-Blind Treatment Period are presented in Table 7; median trough serum concentrations are presented in FIG. 3.

Mean trough levels of estradiol were very similar across treatment groups at Day 1 and increased only in subjects receiving Bio-E Gel® at subsequent time points. At Week 4 and continuing through Week 12, mean trough levels of estradiol were significantly higher among subjects receiving any dose of Bio-E Gel® than among those receiving placebo. Furthermore, the median serum estradiol values increased in a dose-dependent fashion as Bio-E Gel® dose increases (FIG. 3). Mean serum levels of estradiol in the 1.7 g/day and 2.6 g/day groups at Week 4, Week 8, and Week 12 were similar. A recalculation of the 1.7 g/day dose at Day 29 and Day 57 was performed to exclude two extreme outliers. At Day 29 the median estradiol value for the 1.7 g/day dose did not change (23 pg/mL), but the mean ±SD serum estradiol changed from 41.7±73.4 pg/mL to 36.9±48.7 pg/mL while analysis of the serum estradiol at Day 57 changed from 42.7±99.0 pg/mL to 34.5±32.4 pg/mL and the median was unchanged (23.0 pg/mL). With this recalculation there is a dose-dependent increase in the median serum estradiol and an approximately dose-dependent increase in mean serum estradiol concentrations.

TABLE 7

Trough Serum Concentrations of Estradiol Over Time (ITT-Observed Data)

| Hormone [Normal Range][a] | Evaluation | Placebo | Bio-E gel 0.87 g/day | Bio-E gel 1.7 g/day | Bio-E gel 2.6 g/day |
|---|---|---|---|---|---|
| Estradiol [30-300] (pg/mL) | Day 1, N | 136 | 133 | 142 | 68 |
| | Mean ± SD | 12.4 ± 10.6 | 13.2 ± 14.8 | 11.2 ± 10.1 | 9.7 ± 2.9 |
| | Median | 9.0 | 9.0 | 9.0 | 9.0 |
| | Range | 9-75 | 9-140 | 9-95 | 9-27 |
| | Day 29 (Week 4), N | 131 | 130 | 136 | 67 |
| | Mean ± SD | 13.3 ± 18.1 | 30.4 ± 35.3[†] | 41.7 ± 73.4*** | 35.8 ± 33.8* |
| | Median | 9.0 | 19.0 | 23.0 | 27.0 |
| | Range | 9-130 | 9-230 | 9-680 | 9-190 |
| | Day 57 (Week 8), N | 123 | 130 | 132 | 64 |
| | Mean ± SD | 12.3 ± 15.6 | 31.0 ± 35.5[†] | 42.7 ± 99.0** | 41.1 ± 41.9* |
| | Median | 9.0 | 19.0 | 23.0 | 26.0 |
| | Range | 9-140 | 9-210 | 9-1110 | 9-230 |
| | Day 85 (Week 12), N | 128 | 131 | 138 | 67 |
| | Mean ± SD | 14.3 ± 28.0 | 34.3 ± 43.8** | 38.7 ± 42.3*** | 40.8 ± 37.1*** |
| | Median | 9.0 | 20.0 | 23.5 | 29.0 |
| | Range | 9-310 | 9-330 | 9-230 | 9-200 |

[a]Normal range is for premenopausal women (see Section 9.5.4)
[†]$P < 0.05$,
*$P < 0.01$,
**$P < 0.001$,
***$P < 0.0001$ for comparison of LS means for each Bio-E Gel ® treatment group with placebo (Dunnett's test).

Conclusions

For the primary efficacy outcomes of hot flash rate and hot flash severity, statistically significant reductions in daily moderate-to-severe hot flash rate were observed for all doses of Bio-E Gel® compared to the placebo, starting at Week 5 for the 0.87 g/day dose (p=0.0965 at Week 4), and at Week 3 for the 1.7 g/day and 2.6 g/day doses. A clinically meaningful reduction in hot flash rate compared to the placebo-treated group was first seen at Week 5, 4, and 3 for study groups receiving 0.87 g/day Bio-E gel, 1.7 g/day Bio-E Gel® and 2.6 g/day Bio-E gel, respectively. Reductions in hot flash severity were statistically significantly different from placebo treatment by Week 5 for the 0.87 g/day dose (p=0.0714 at Week 4), by Week 3 for the 1.7 g/day, and by Week 2 for the 2.6 g/day doses of Bio-E gel. Reductions in daily moderate-to-severe hot flash rate that were both clinically meaningful and statistically significant and reductions in hot flash severity that were statistically significant were maintained from time of onset through Week 12 for all Bio-E Gel® dose groups.

Regarding estradiol concentrations, treatment with increasing doses of Bio-E Gel® showed a dose-dependent increase in median trough concentrations of estradiol and an approximately dose-dependent increase in mean concentrations of estradiol. The effects of Bio-E Gel® on vasomotor symptoms were dose-related and were consistent with the dose-related increases observed in median serum concentrations of estradiol.

Efficacy outcomes in this study support 0.87 g/day as the lowest effective dose of Bio-E Gel® for the treatment of vasomotor symptoms and vulvovaginal atrophy symptoms in postmenopausal women.

Safety:

The general findings of this study with respect to the safety of Bio-E Gel® was that it was well-tolerated locally, with few subjects experiencing application site reactions. Bio-E Gel® did not produce any adverse events that were not already well-recognized for estrogen drug products used for the treatment of vasomotor and vulvovaginal symptoms associated with menopause.

The overall incidence of treatment-emergent adverse events increased with increasing dose of Bio-E Gel® (59% to 68% across the three doses) and was slightly higher than the incidence in the placebo group (56%). Treatment-emergent adverse events that occurred in >5% of subjects during 12-week treatment for all Bio-E Gel® doses were nausea, peripheral edema, breast tenderness, metrorrhagia, vaginal discharge, nipple pain, endometrial hyperplasia, nasopharyngitis, and upper respiratory tract infection.

Study Conclusions:

The results of this study demonstrate that Bio-E Gel® effectively reduces vasomotor and vulvovaginal symptoms associated with menopause. Given the efficacy of the low dose (0.87 g/day) of Bio-E Gel® along with its ability to significantly increase estradiol levels and comparative safety relative to the higher doses (1.7 g/day and 2.6 g/day), 0.87 g/day Bio-E Gel® is considered to be the lowest effective dose for the treatment of vasomotor symptoms and vulvovaginal symptoms in postmenopausal women.

While the specification describes particular embodiments of the present invention, those of ordinary skill can devise variations of the present invention without departing from the inventive concept. Thus, the invention described and claimed herein is not to be limited in scope by the specific embodiments disclosed herein, since these embodiments are intended as illustrations of several aspects of the invention. Any equivalent embodiments are intended to be within the scope of the invention. Indeed, various modifications of the invention in addition to those shown and described herein will become apparent to those skilled in the art from the foregoing description. Such modifications are also intended to fall within the scope of the appended claims.

What is claimed is:

1. A method for treating hot flashes, which comprises administering to a subject in need of such treatment a topical or transmucosal formulation daily over a period of at least five weeks, the formulation comprising:

| | |
|---|---|
| Estradiol | 0.06% |
| Ethanol, Dehydrated | 46.28% |
| Propylene Glycol | 6% |
| Diethylene glycol monoethyl ether | 5% |
| Carbomer 940 | 1.20% |
| Triethanolamine | 0.35% |
| Ion Exchange Purified Water q. ad. | 100% | wherein the daily administration of the formulation is in an amount of from about 0.75 g to about 1 g.

2. The method of claim 1, wherein the daily administration of the formulation is in an amount of from about 0.85 g to about 0.9 g.

3. The method of claim 1, wherein the subject is female and the amount of estradiol which is administered daily is effective to produce a serum estradiol level in the subject of between about 25 pg/ml to about 50 pg/ml, and wherein the estimated nominal daily estradiol dose provided by the formulation is from about 10 to about 15 micrograms.

4. The method of claim 3, wherein the subject is menopausal or is estrogen deficient.

* * * * *